United States Patent [19]

Takamatsu

[11] 3,977,053
[45] Aug. 31, 1976

[54] SLIDE FASTENER STRINGER

[75] Inventor: Ikuo Takamatsu, Uozu, Japan

[73] Assignee: Yoshida Kogyo Kabushiki Kaisha, Japan

[22] Filed: Sept. 24, 1974

[21] Appl. No.: 508,882

[30] Foreign Application Priority Data
Oct. 20, 1973  Japan.................. 48-121824[U]

[52] U.S. Cl. ................. 24/205.16 R; 24/205.13 R
[51] Int. Cl.² ................................. A44B 19/40
[58] Field of Search ............ 24/205.13 R, 205.16 D, 24/205.16 C, 205.16 R, 205.13 C, 205.13 D

[56] References Cited
UNITED STATES PATENTS

| | | | |
|---|---|---|---|
| 1,902,416 | 3/1933 | Norton | 24/205.13 R |
| 2,048,544 | 7/1936 | Fritts | 24/205.13 R |
| 2,263,920 | 11/1941 | Dau | 24/205.16 R |
| 2,389,565 | 11/1945 | Taberlet | 24/205.13 R |
| 2,583,035 | 1/1952 | Winterhalter | 24/205.13 R |
| 2,629,911 | 3/1953 | Macy | 24/205.13 D |
| 3,129,478 | 4/1964 | Morin | 24/205.13 R |
| 3,175,028 | 3/1965 | Waldes | 24/205.16 R |
| 3,490,098 | 1/1970 | Frohlica | 24/205.13 D |
| 3,568,266 | 3/1971 | Uhrig | 24/205.13 R |
| 3,704,490 | 12/1972 | Hansen | 24/205.13 D |
| 3,710,429 | 1/1973 | Spindler | 24/205.13 C |

FOREIGN PATENTS OR APPLICATIONS

| | | | |
|---|---|---|---|
| 851,946 | 10/1960 | United Kingdom | 24/205.13 D |

*Primary Examiner*—Bernard A. Gelak
*Attorney, Agent, or Firm*—Bucknam and Archer

[57] ABSTRACT

In a slide fastener stringer having a row of discrete fastener elements arranged along one longitudinal edge thereof and each comprising a coupling head at its front end and a pair of parallel spaced legs extending rearwardly from the coupling head, the rear end portions of the legs of each fastener element are flattened into plate-like shape, with steps formed between these flattened rear end portions of the respective legs and their remaining portions. The flattened rear end portions of the legs of each fastener element are embedded into the stringer tape from both surfaces thereof, to such a degree that the outer surfaces of the flattened rear end portions are flush with the corresponding surfaces of the stringer tape, thereby providing slideways for the marginal guide flanges of a slider traveling along the fastener elements.

2 Claims, 2 Drawing Figures

SLIDE FASTENER STRINGER

BACKGROUND OF THE INVENTION

This invention relates generally to slide fasteners, and more specifically to the improved construction of a stringer for slide fasteners of the type having a row of discrete fastener elements of substantially U-shaped configuration affixed to one of the longitudinal edges of a stringer tape for mating interengagement with identical fastener elements of a companion stringer.

There has been known a stringer construction for the slide fasteners of the type above defined wherein those ends of a pair of legs or shanks of each fastener element remote from its coupling head are so deformed as to provide guideways for the marginal guide flanges of a slider traveling along rows of such interlockable fastener elements. While the movement of the slider along the fastener elements is certainly made smoother thanks to this known stringer construction, the stepped configuration of the legs of each fastener element necessitates a significantly increased dimension for the fastener element in a direction perpendicular to the plane of the stringer tape. Such "thick" fastener elements are of course aesthetically unappealing.

If this disadvantage is circumvented by lessening the thickness of the fastener elements, then the steps between the deformed end portions of the legs of each element and their remaining portions must correspondingly be decreased in height. The steps of such decreased height may become unable to definitely engage the marginal guide flanges of the slider from within the slider body, so that the slider will tend to come off the rows of fastener elements whenever lateral pulling forces are exerted from both sides of the slide fastener during or after the fastener closing movement of the slider.

SUMMARY OF THE INVENTION

It is, therefore, an object of this invention to provide an improved stringer for the slide fasteners of the aforementioned type wherein the thickness of the respective fastener elements is materially reduced without any corresponding decrease in the height of the steps between the deformed end portions and the remaining portions of the legs of each fastener element.

Another object of the invention is to provide a slide fastener stringer of the above described character which is easily and inexpensively manufacturable.

In order to accomplish these objects and others which will be hereinafter made apparent, this invention contemplates the provision of a slide fastener stringer having a row of fastener elements lying along one longitudinal edge of a stringer tape and each having a coupling head at its front end and a pair of legs extending rearwardly from the coupling head in spaced parallelism. The rear end portions of the legs of each fastener element are flattened slideways for the marginal guide flanges of a slider for use with a pair of such stringers. The flattened rear end portions of the legs of each fastener element are buried into the stringer tape from both surfaces thereof, only to such an extent that the outer surfaces of the respective flattened rear end portions are held in substantially coplanar relationship to the corresponding surfaces of the stringer tape.

It is possible in this manner to significantly reduce the thickness of each fastener element without decreasing the height of the steps formed between the flattened rear end portions and the remaining portions of the legs of the fastener element. The flattened rear end portions can be easily formed and buried into the stringer tape as by ultrasonic welding operation if each fastener element is made of a thermoplastic synthetic resin monofilament.

The features which are believed to be novel and characteristic of this invention are set forth with particularity in the appended claims. The invention itself, however, as well as the further objects and advantages thereof, will be best understood from the following description taken in conjunction with the accompanying drawings.

DESCRIPTION OF THE PREFERRED EMBODIMENT

Figure 1:
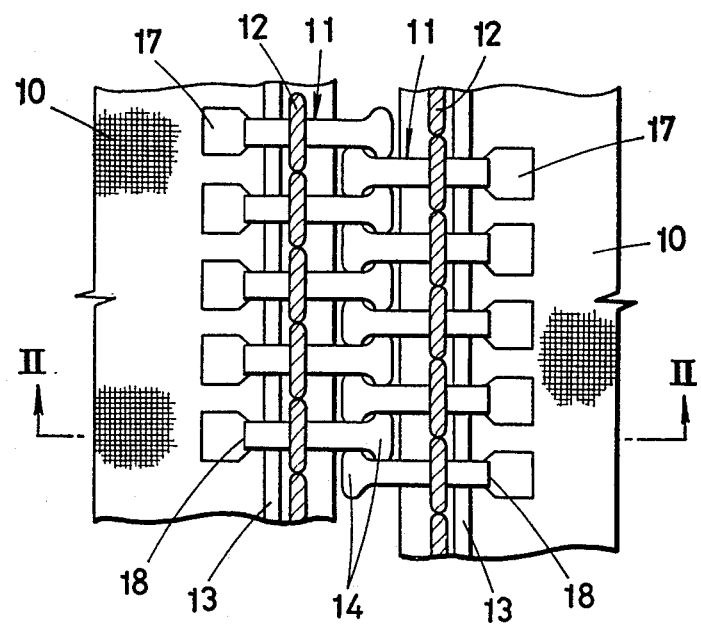
FIG. 1 is a partial top plan view of a pair of slide fastener stringers constructed in accordance with the novel concepts of this invention.
Figure 2:
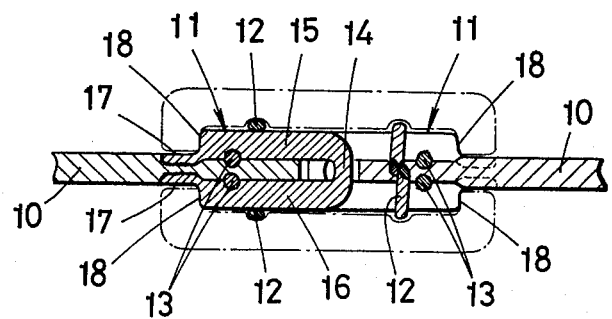
FIG. 2 is a sectional view taken along the plane of line II—II in FIG. 1.

In the pair of slide fastener stringers illustrated in FIGS. 1 and 2 to represent one of the specific adaptations of this invention, the reference numeral 10 denotes stringer tapes each carrying a longitudinal row of uniformly spaced fastener elements 11 of discrete type along the adjacent front edge thereof. In this particular adaptation of the invention, the matingly interengageable rows of fastener elements 11 are stitched onto the opposed front edges of the respective stringer tapes by threads 12, although the stitching of the fastener elements is not of absolute necessity. Arranged longitudinally of the respective stringer tapes 10 on both surfaces thereof are beads 13 which may be in the form of fabric cords or synthetic resin monofilaments adapted to carry the respective rows of fastener elements 11 with preassigned pitch distance.

As best shown in FIG. 2, each of the fastener elements 11 is of generally U-shaped configuration, comprising a coupling head 14 at its front end and a pair of parallel spaced legs 15 and 16 extending rearwardly from the coupling head 14, with the plane of the legs 15 and 16 arranged perpendicular to the plane of the stringer tape 10. Each fastener element can, for the purposes of this invention, be most suitably fabricated of a monofilamentary thermoplastic synthetic resin.

With reference to both FIGS. 1 and 2, the corresponding rear end portions of the legs 15 and 16 of each fastener element 11 are flattened into plate-like shape, as indicated by the numeral 17 in the drawings, to provide slideways for the slider represented by the dot-and-dash lines in FIG. 2. Steps 18 are formed resultantly between the flattened rear end portions 17 of the respective legs 15 and 16 and their remaining portions. Furthermore, these flattened rear end portions of the legs of each fastener element are buried into the stringer tape 10 from both surfaces thereof, to such an extent that the outer surfaces of the respective flattened rear end portions are in substantially coplanar relationship to the corresponding surfaces of the stringer tape. The term "substantially coplanar relationship" is used herein principally to allow for some manufacturing tolerances that are permissible from the standpoint of the objects of the invention.

Since each fastener element 11 is formed of a monofilamentary thermoplastic synthetic resin as previously mentioned, the flattened rear end portions 17 of its legs 15 and 16 may preferably be buried into the stringer tape 10 simultaneously as they are so deformed under application of heat and pressure as by the conventional technique of ultrasonic welding. It is also possible, however, that these two operations be effected separately.

The phantom slider seen in FIG. 2 may be of the well known type comprising a pair of similar wings or plate members interconnected by a neck at their upper ends. Each wing is provided with marginal guide flanges which cooperate with the neck to form the usual Y-shaped guide channel for guiding the rows of fastener elements 11 therethrough. Hence, as this slider is pulled along the rows of fastener elements 11 to couple or uncouple the pair of stringers shown in FIGS. 1 and 2, its marginal guide flanges move in smooth sliding contact with the aforesaid slideways formed by the flattened rear end portions 17 of the legs 15 and 16 of the respective fastener elements.

It should be noted that although each fastener element 11 is of extremely small thickness as clearly seen in FIG. 2, the steps 18 can be of sufficient height to positively engage the marginal guide flanges of the slider because the flattened rear end portions 17 of the respective legs 15 and 16 are embedded in the stringer tape 10. Therefore, if lateral pulling forces are exerted on this slide fastener from both sides thereof during or after the fastener closing movement of the slider, there is substantially no possibility of the slider coming off the rows of fastener elements 11.

Although the slide fastener stringer according to the invention has been shown and described hereinbefore in very specific aspects thereof to enable those skilled in the art to practice the invention, it will be apparent that the disclosure hereof is meant only to illustrate and explain and not to impose limitations upon the invention. Various modifications may obviously be contemplated and resorted to by the specialists without departing from the scope of the invention as sought to be defined by the following claims.

What is claimed is:

1. In a slide fastener having a pair of opposed stringer tapes each bearing a row of fastener elements and a slider moveable along such rows of fastener elements to put same into and out of interengagement, the improvement which comprises each of said fastener elements including a coupling head at its front end and a pair of substantially parallel spaced legs extending rearwardly from said coupling head, flattened portions formed at the rear ends of said legs of each of said fastener elements to provide slideways for a slider, said flattened portions being buried into said stringer tape from both surfaces thereof to such an extent that the outer surfaces of the respective flattened portions are in substantially coplanar relationship to corresponding surfaces of said stringer tape adjacent said flattened portions, and steps formed between said flattened portions of the respective legs of each of said fastener elements and the remaining portions thereof, and marginal flanges on said slider disposed for sliding contact engagement with said slideways.

2. A slide fastener stringer as set forth in claim 1, further including at least a row of stitches adapted to secure said fastener elements to said stringer tape.

* * * * *